United States Patent
Jackson et al.

(10) Patent No.: US 9,420,976 B2
(45) Date of Patent: Aug. 23, 2016

(54) SYSTEMS AND METHODS FOR OPTIMIZED SOURCE COLLIMATION

(71) Applicant: General Electric Company, Schenectady, NY (US)

(72) Inventors: John Irvin Jackson, Brookfield, WI (US); Holly Ann McDaniel, Waukesha, WI (US); Grant Morey Stevens, Cedarburg, WI (US); Bradley Jay Gabrielse, Brookfield, WI (US); Dominic Joseph Crotty, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 212 days.

(21) Appl. No.: 14/219,245

(22) Filed: Mar. 19, 2014

(65) Prior Publication Data

US 2015/0265226 A1    Sep. 24, 2015

(51) Int. Cl.
| | |
|---|---|
| *A61B 6/03* | (2006.01) |
| *G21K 1/02* | (2006.01) |
| *G21K 1/04* | (2006.01) |
| *A61B 6/06* | (2006.01) |
| *A61B 6/00* | (2006.01) |

(52) U.S. Cl.
CPC . *A61B 6/032* (2013.01); *A61B 6/06* (2013.01); *A61B 6/54* (2013.01); *A61B 6/542* (2013.01); *A61B 6/545* (2013.01); *G21K 1/04* (2013.01)

(58) Field of Classification Search
CPC .......... A61B 6/032; A61B 6/035; A61B 6/06; A61B 6/54; A61B 6/542; A61B 6/545
USPC ...................... 378/16, 20, 150–153
See application file for complete search history.

(56) References Cited

U.S. PATENT DOCUMENTS

| | | | |
|---|---|---|---|
| 5,170,439 A | 12/1992 | Zeng et al. | |
| 5,706,325 A | 1/1998 | Hu | |
| 6,014,419 A | 1/2000 | Hu | |
| 6,137,858 A * | 10/2000 | Horiuchi | A61B 6/032 250/336.1 |
| 6,320,929 B1 * | 11/2001 | Von Der Haar | A61B 6/032 378/15 |
| 6,339,636 B1 * | 1/2002 | Ogawa | A61B 6/032 378/146 |
| 6,445,761 B1 | 9/2002 | Miyazaki et al. | |
| 6,463,121 B1 * | 10/2002 | Milnes | A61B 6/4482 378/62 |
| 6,501,828 B1 * | 12/2002 | Popescu | A61B 6/06 378/145 |
| 6,546,067 B2 | 4/2003 | Aradate et al. | |
| 6,568,851 B2 * | 5/2003 | Saito | A61B 6/032 378/19 |
| 6,574,299 B1 * | 6/2003 | Katsevich | G06T 11/006 378/15 |
| 6,619,839 B2 * | 9/2003 | Yoshimura | A61B 6/0478 378/195 |

(Continued)

Primary Examiner — Allen C. Ho
(74) Attorney, Agent, or Firm — Dean D. Small; The Small Patent Law Group, LLC

(57) ABSTRACT

An imaging system is provided including an adjustable source collimator, an input unit, and a processing unit. The adjustable source collimator is configured to be interposed between an X-ray source and an object to be imaged, and is adjustable between plural settings corresponding to different amounts of collimation of rays from the X-ray source. The input unit is configured to obtain an input identifying a portion to be imaged of the object. The processing unit is operably coupled to the input unit and the adjustable source collimator, and configured to obtain the input. The processing unit is also configured to determine a prescribed collimation configuration to perform a scan of the portion to be imaged based on the input, the prescribed collimation configuration having a corresponding scanning volume that includes the portion to be imaged.

20 Claims, 9 Drawing Sheets

(56) References Cited

U.S. PATENT DOCUMENTS

| | | | | |
|---|---|---|---|---|
| 6,771,733 B2 * | 8/2004 | Katsevich | A61B 6/032 378/15 |
| 6,834,097 B2 * | 12/2004 | Yamazaki | A61B 6/488 378/19 |
| 6,850,585 B2 * | 2/2005 | Hsieh | A61B 6/481 378/15 |
| 6,928,137 B2 * | 8/2005 | Bruder | A61B 6/032 378/4 |
| 6,990,170 B2 * | 1/2006 | Sugihara | A61B 6/032 378/15 |
| 6,990,175 B2 * | 1/2006 | Nakashima | A61B 6/032 378/101 |
| 7,010,079 B2 * | 3/2006 | Katsevich | A61B 6/032 378/15 |
| 7,076,019 B2 * | 7/2006 | Hagiwara | A61B 6/032 378/16 |
| 7,113,569 B2 * | 9/2006 | Okumura | A61B 6/032 378/150 |
| 7,113,570 B2 * | 9/2006 | Toth | A61B 6/032 378/150 |
| 7,197,105 B2 * | 3/2007 | Katsevich | A61B 6/4441 378/4 |
| 7,409,034 B2 * | 8/2008 | Gohno | A61B 6/032 378/15 |
| 7,508,903 B2 * | 3/2009 | Nishide | A61B 6/06 378/15 |
| 7,515,678 B2 * | 4/2009 | Hsieh | A61B 6/032 250/370.09 |
| 7,526,065 B2 * | 4/2009 | Hardesty | A61B 6/542 378/145 |
| 7,580,502 B2 * | 8/2009 | Dalpiaz | A61B 6/14 378/38 |
| 7,583,775 B2 * | 9/2009 | Ozaki | G21K 1/04 250/370.11 |
| 7,881,423 B2 * | 2/2011 | Tsuyuki | A61B 6/032 378/207 |
| 7,983,385 B2 * | 7/2011 | Heuscher | A61B 6/032 378/11 |
| 8,005,187 B2 * | 8/2011 | Suzuki | A61B 6/032 378/19 |
| 8,009,794 B2 * | 8/2011 | Partain | A61B 6/032 378/150 |
| 8,031,830 B2 | 10/2011 | Nakanishi | |
| 8,094,775 B2 * | 1/2012 | Noshi | A61B 6/032 378/15 |
| 8,170,640 B2 * | 5/2012 | Kiraly | G06T 3/0037 382/128 |
| 8,184,775 B1 * | 5/2012 | Fan | A61B 6/4085 378/147 |
| 8,213,568 B2 * | 7/2012 | Heuscher | A61B 6/06 378/15 |
| 8,218,721 B2 * | 7/2012 | Raupach | A61B 6/032 378/150 |
| 8,396,184 B2 * | 3/2013 | Shinno | A61B 6/032 378/5 |
| 8,553,833 B2 * | 10/2013 | Flohr | A61B 6/032 378/15 |
| 8,897,413 B2 * | 11/2014 | Heuscher | A61B 6/032 378/15 |
| 8,964,942 B2 * | 2/2015 | Dafni | G01T 1/2985 378/150 |
| 9,198,626 B2 * | 12/2015 | Heuscher | A61B 6/032 |
| 9,259,191 B2 * | 2/2016 | Noo | G21K 1/02 |
| 9,295,434 B2 * | 3/2016 | Herold | A61B 6/032 |
| 9,332,946 B2 * | 5/2016 | Heuscher | A61B 6/032 |
| 2003/0068005 A1 | 4/2003 | Yamazaki | |
| 2004/0141581 A1 | 7/2004 | Bruder et al. | |
| 2004/0174960 A1 | 9/2004 | Hsieh et al. | |
| 2005/0053188 A1 | 3/2005 | Gohno | |
| 2006/0034417 A1 | 2/2006 | Katsevich | |
| 2007/0053478 A1 | 3/2007 | Tsuyuki et al. | |

* cited by examiner

SYSTEMS AND METHODS FOR OPTIMIZED SOURCE COLLIMATION

BACKGROUND OF THE INVENTION

The subject matter disclosed herein relates generally to systems and methods for collimation of rays from a source toward an object to be imaged.

In computed tomography (CT) imaging, an X-ray source may be rotated around an object to obtain imaging information. A collimator may be used to direct radiation from the source to the object to be imaged, and to limit radiation directed to the object to a desired field of view. Conventional CT systems may use a relatively small, non-adjustable collimator to acquire imaging information over a rotation of the source around the object to be imaged.

Traditionally, volumetric CT scanners have generated image data within relatively small cylindrical volumes, and/or cylindrical volumes of a single, non-adjustable size. To the extent a single volume was not large enough, additional cylindrical volumes could be selected and specified by a user, as the decision to add an additional rotation is a relatively straightforward decision, and does not require substantial computation requirements. However, more recent CT scanner designs provide larger, adjustable collimations. Further, more recent CT scanner designs provide for scanning volumes having shapes different than cylindrical. For example, image data may be additionally generated in cone-shaped regions above and below a cylinder. With differently shaped volumes available as well as adjustable volume sizes, the scanning geometry quickly becomes quite complicated. Further, multiple available combinations of scanning volumes and positions provide a large number of possible choices. The wide number of available combinations of volume number, volume length, volume spacing, as well as the complex geometries of scanning volumes make it difficult to readily identify optimal or preferable options among the myriad available choices.

BRIEF DESCRIPTION OF THE INVENTION

In one embodiment, an imaging system is provided that includes an adjustable source collimator, an input unit, and a processing unit. The adjustable source collimator is configured to be interposed between an X-ray source and an object to be imaged, and is adjustable between plural settings corresponding to different amounts of collimation of rays from the X-ray source. The input unit is configured to obtain an input corresponding to a portion of the object to be imaged. The processing unit is operably coupled to the input unit and the adjustable source collimator, and configured to obtain the user input. The processing unit is also configured to determine a prescribed collimation configuration to perform a scan of the portion to be imaged. The prescribed collimation configuration has a corresponding scanning volume that includes the portion to be imaged.

In another embodiment, a method is provided for selecting a source collimation configuration for an object to be imaged. The method includes receiving, at an input unit, an input (e.g., a user input from a user) corresponding to a portion of the object to be imaged. The method also includes determining, with a processing unit, a prescribed collimation configuration to perform a scan of the portion to be imaged. The prescribed collimation configuration has a corresponding scanning volume that includes the portion to be imaged.

In another embodiment, a tangible and non-transitory computer readable medium is provided for selecting a source collimation configuration for an object to be imaged. The tangible and non-transitory computer readable medium includes one or more computer software modules configured to direct one or more processors to receive an input corresponding to a portion of the object to be imaged. The one or more computer software modules are also configured to direct the one or more processors to determine, automatically, a prescribed collimation configuration to perform a scan of the portion to be imaged, the prescribed collimation configuration having a corresponding scanning volume that includes the portion to be imaged.

DETAILED DESCRIPTION OF THE INVENTION

Figure 1:
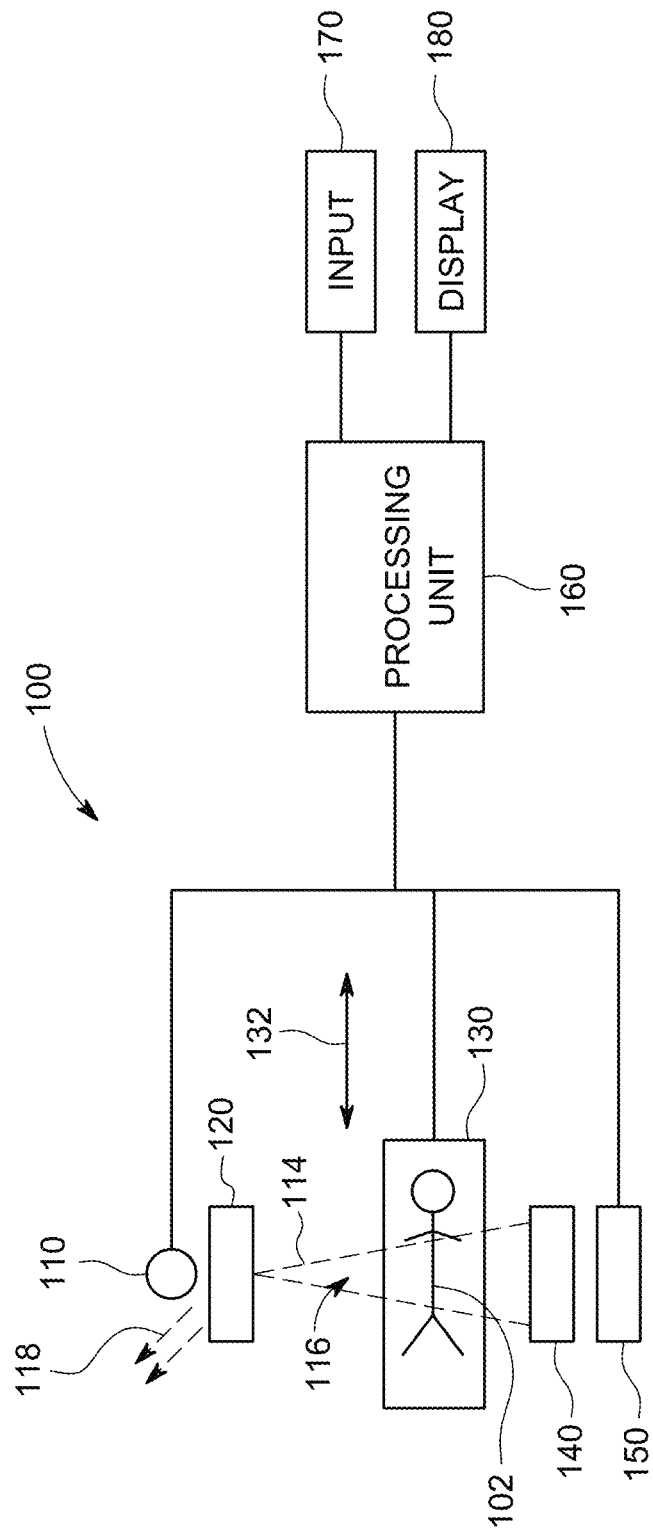
FIG. 1 is a schematic block diagram illustrating an imaging system in accordance with an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for selection of collimation settings or configurations to be used for imaging. In various embodiments, an anatomic location may be specified. For example, two or more points (e.g., a start point and end point corresponding to boundaries defining a desired imaging region) may be specified by a user. As another example, one or more anatomic locations may be determined using an anatomic segmentation, for example using software configured to identify particular portions of anatomy from a scout scan. As another example, a volume of data, such as data generated from a low-dose localizer scan, may be used in selecting or determining a location or portion to be imaged. As another example, locations may be specified by a protocol for a particular procedure (e.g., a cardiac procedure). In various embodiments, a processor is configured (e.g., programmed) to determine a collimation configuration that satisfies one or more criteria (e.g., a collimation that provides a minimum or reduced total collimation length, a collimation that provides a minimum or reduced radiation dosage, or a collimation the provides a minimum or reduced number of table positions used during a scan, among others) while providing sufficient coverage of the specified anatomic region, portion, or location based at least in part on geometric constraints (e.g., size of gantry, available collimation lengths or sizes). The processor, for example, may determine a scanning volume provided by at least one of a list of collimation configurations, and then select a collimation configuration that provides a scanning volume including a target region corresponding to the anatomic region to be imaged while satisfying one or more additional criteria (e.g., reduce or minimize number of slabs or rotations, reduce or minimize radiation dosage, or the like). The collimation configuration may be selected to satisfy one or more image quality conditions or constraints. For example, a minimum signal-to-noise ratio or other metric may be employed to constrain selection of the collimation configuration. In various embodiments, a collimation configuration may be selected as a function of a desired reconstructed image volume and/or one or more image quality constraints.

Various embodiments provide improved imaging. For example, a collimation configuration satisfying one or more criteria may be selected. A technical effect of at least one embodiment includes improved imaging, for example by improving selection of a collimation configuration to satisfy one or more criteria. A technical effect of at least one embodiment includes reducing effort required by a user to specify a collimation configuration and/or reducing or eliminating human error in collimation configuration selection. A technical effect of at least one embodiment is to provide selection or determination of collimation configuration as a function of a desired image reconstruction volume and/or one or more image quality constraints. A technical effect of at least one embodiment is to provide optimal or improved levels of radiation dosage for a scan.

FIG. 1 illustrates an imaging system 100 in accordance with an embodiment. The imaging system 100 may be configured, for example, to perform computed tomography (CT) scanning of a subject, such as a human or animal patient. As seen in FIG. 1, the depicted imaging system 100 includes an X-ray source 110, an adjustable source collimator 120, a table 130, a detector collimator 140, a detector 150, a processing unit 160, an input unit 170, and a display unit 180. It may be noted that various embodiments may include additional components, or may not include all of the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity. For example, the display unit 180 and the input unit 170 may share or be incorporated into a common physical entity (e.g., touchscreen). In the illustrated embodiment, the imaging system 100 is configured to perform CT imaging of an object 102. For example, the object 102 may be a human patient, and the imaging system 100 may perform a CT scan of one or more specified portions of the object 102 (e.g., heart, lungs, head, or region identified by boundaries input by a user, among others).

Generally, X-rays 114 from the X-ray source 110 are guided to the object 102 through the adjustable source collimator 120, which is configured to allow X-rays 114 within a desired field of view (FOV) 116 to pass through to the object 102 while blocking other X-rays 118. The table 130 supports the object 102 in a desired position. X-rays 114 that pass through the object 102 are attenuated by the object 102 and received by the detector collimator 140, which is configured to guide attenuated X-rays to the detector 150, which detects the attenuated X-rays and provides imaging information to the processing unit 160. The processing unit 160 may then reconstruct an image of the scanned portion of the object 102 using the imaging information provided by the detector 150. In the illustrated embodiment, the processing unit 160 is also configured to select a configuration for the adjustable source collimator 120 to cover a desired portion of the object 102. The display unit 180 in the illustrated embodiment may be configured for example, to display a collimation configuration selected by the processing unit 160, to display a scanning volume covered by the collimation configuration selected by the processing unit 160, and/or to display an image, such as a scout image obtained prior to collection of imaging information, or, as another example, an image reconstructed using imaging information from the detector 150. The depicted input unit 170 is configured to obtain input corresponding to a portion or region of the object 102 that is desired to be imaged, with the processing unit 160 using the input to determine a collimation configuration.

As used herein, a collimation configuration may specify or describe characteristics or aspects of the source collimation to be employed over a scan. For example, the collimation configuration specifies the total number of slabs of information to be obtained, and the length of the slab or slabs used during the scan The collimation configuration may also specify the spacing of slabs relative to each other for collimation configurations having two or more slabs. As another example, in some embodiments, the collimation configuration may specify a source intensity (e.g., tube current) employed for each slab.

In the illustrated embodiment, the X-ray source 110 is configured to rotate about the object 102 and table 130. For example, the X-ray source 110, adjustable source collimator 120, detector collimator 140 and detector 150 may be positioned about a gantry bore (not shown in FIG. 1 for clarity of illustration) that rotates about the table 130. As the X-ray source 110 rotates about the object 102, X-rays received by the detector 150 during one complete rotation provide a 360 degree view of X-rays that have passed through the object 102. As used herein, one complete rotation of the X-ray source 110 about the object 102 corresponds to a slab of information. The slab, in turn, may include a number of slices along the length of the slab, with each slice corresponding to a row of pixels in the detector 150.

Figure 2:
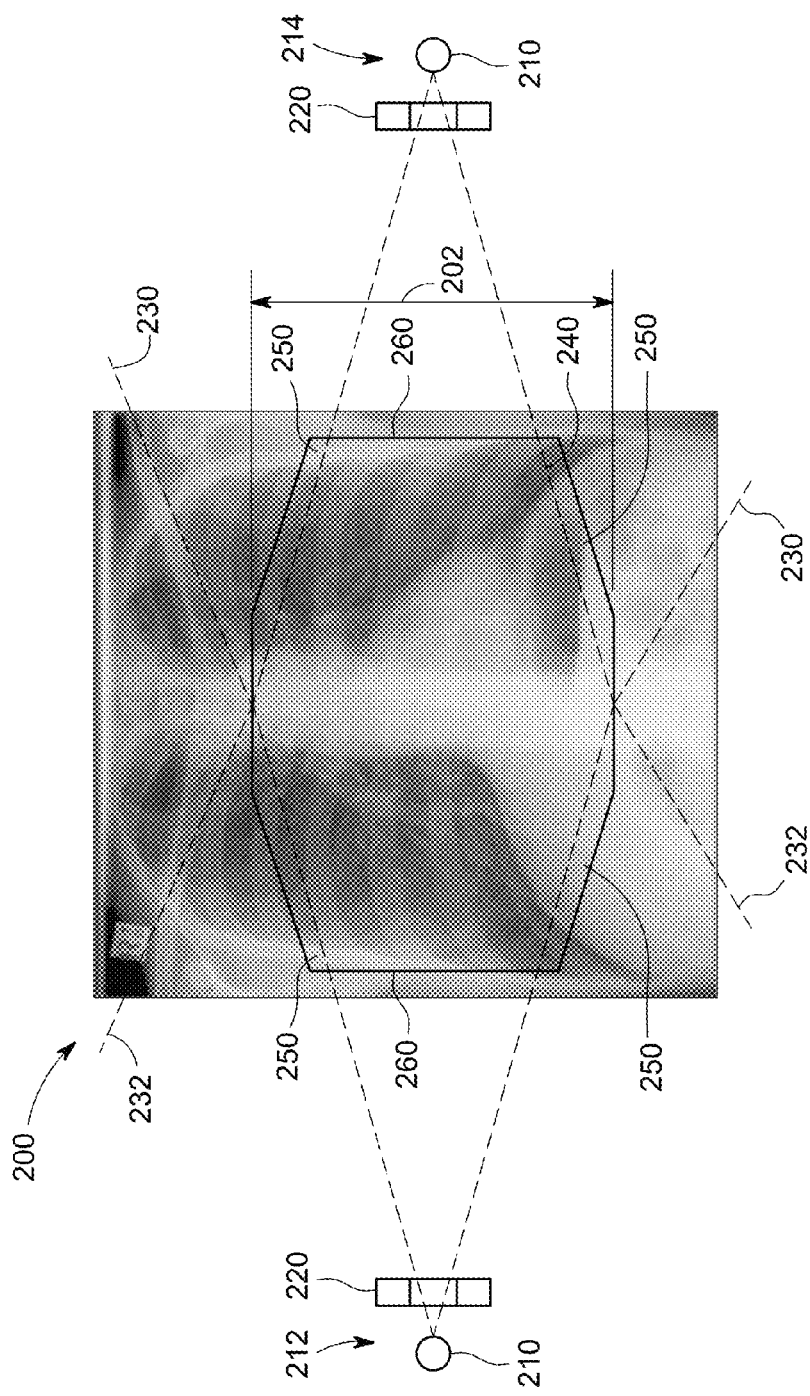
FIG. 2 illustrates an example scanning volume in accordance with an embodiment.
Figure 3:
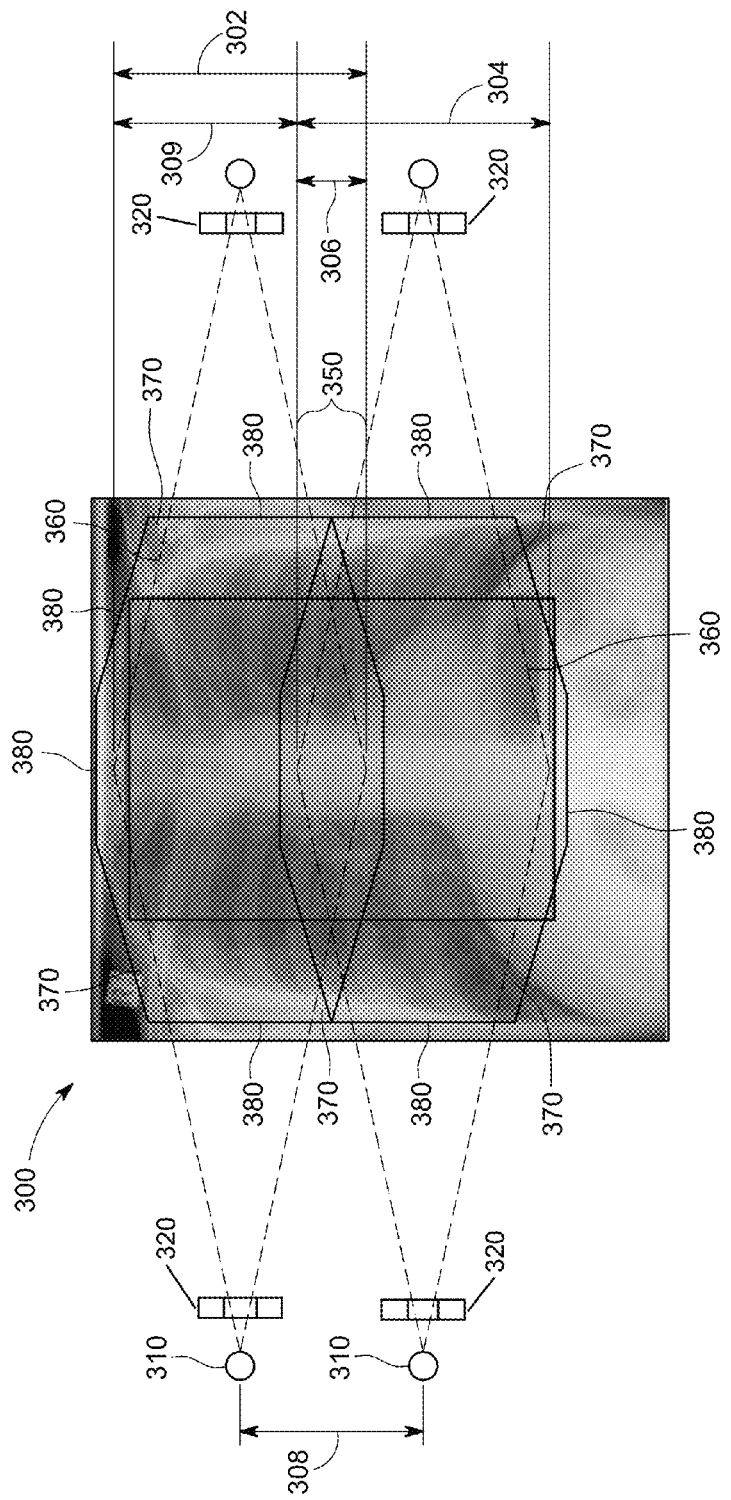
FIG. 3 illustrates an example scanning volume in accordance with an embodiment.
Figure 4:
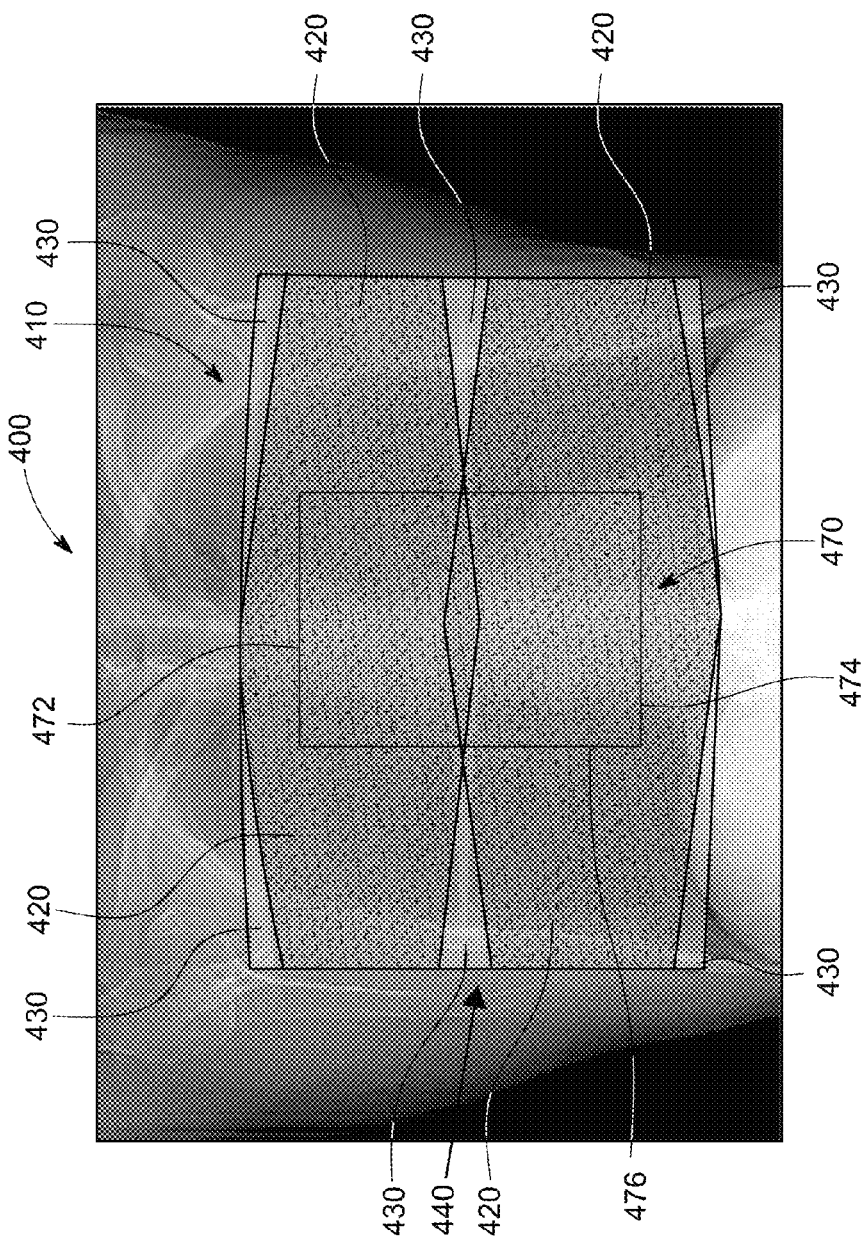
FIG. 4 illustrates an example scanning volume in accordance with an embodiment.

FIGS. 2-4 provide example depictions of scanning volumes obtainable using the X-ray source 110 and adjustable source collimator 120. FIG. 2 depicts a scout image 200 of a torso with various scanning volumes overlayed on the scout image 200. A scout image 200 may be obtained by performing a scout scan at relative low radiation dosages or exposures. The scout image 200 is not generally used for imaging, but instead provides a preliminary view of a portion of a patient to be imaged, for example, for use in positioning a patient. In FIG. 2, scanning volumes corresponding to a single rotation or slab are depicted. X-rays from an x-ray source 210 pass through a source collimator 220 to define a Field of View (FOV). The length of the object within the FOV defines a slab length 202. The collimator 220 is adjustable to provide for adjustment of the slab length 202. By allowing a wider angle of X-rays to pass from the x-ray source 210, the slab length 202 may be increased. Conversely, by allowing a narrower angle of X-rays to pass from the x-ray source 210, the slab length 202 may be reduced.

In FIG. 2 the x-ray source 210 rotates about an object (or portion thereof to be imaged). As seen in FIG. 2, the x-ray source 210 generally rotates in a plane that is normal to page (or rotates into and out of the page). At the depicted point 212 during the rotation of the x-ray source 210 about the object, X-rays from the x-ray source 210 pass through the source collimator 220 to define an FOV 230. An FOV 232 is similarly provided when the x-ray source 210 is at the depicted point 214, which is located 180 degrees from the point 212. The overlap of the FOV 230 and the FOV 232 corresponds to a primary scanning volume 240. The primary scanning volume 240 includes the volume covered by a 360 degree rotation of the overlapping portions of the depicted FOV 230 and FOV 232. The primary scanning volume 240 thus appears as diamond or rhombus shaped in two dimensions, and discus-shaped in three-dimensions.

Portions of the object with the primary scanning volume 240 are the portions of the object which are visible to a detector receiving x-rays from the x-ray source 210 during a complete rotation (360 degrees), or portions of the object for which the detector receives 360 degrees of coverage of attenuated x-rays from the x-ray source 210. Portions of the object outside of the primary scanning volume 240 are those portions for which the detector does not receive 360 degree coverage of attenuated x-rays from the x-ray source 210. However, it may be noted that less than 360 degrees of coverage may be required to provide clinically useful imaging information. While this information may be of lower quality than imaging information from the primary scanning volume 240, or more susceptible to noise or motion related artifacts, the information may be sufficient for some portions outside of the primary scanning volume 240 to be reconstructed in a clinically useful image. The portions of the scanned volume outside of the primary scanning volume 240 that provide clinically useful imaging information are depicted as shoulder regions 250 in FIG. 2. The shoulder regions 250, along with the portions of the primary scanning volume 240 corresponding to the object, together form a scanning volume 260. The scanning volume 260 includes those portions of the object for which clinically useful imaging information may be obtained by a slab corresponding to the collimation configuration of FIG. 2. It may be noted that neither the primary scanning volume 240 nor the scanning volume 260 are rectangular in shape, but instead each are generally tapered away from the center of the object.

FIG. 3 depicts a scout image 300 of a torso with various scanning volumes overlayed on the scout image 300. In FIG. 3, two slabs are depicted. A first slab length 302 of imaging information is obtained in a first rotation of an x-ray source 310, and a second slab length 304 of imaging information is obtained in a second rotation after the x-ray source 310 has been translated axially relative to the object (e.g., by an axial translation of a bed or support). The combined slab length or collimation length as used herein for a given configuration is the sum of individual slab lengths for all slabs of the configuration. It may be noted that the overall coverage of the collimation configuration may be less than sum of lengths for each slab or total collimator length due to overlap between the slabs.

As seen in FIG. 3, the first slab length 302 and second slab length 304 define an overlap 306, so that the total length covered by the first slab length 302 and the second slab length 304 (or total coverage of the collimation configuration) is less than the sum of the first slab length 302 and the second slab length 304. In FIG. 3, the slabs are spaced at a slab spacing 308. The slab spacing 308 may also be understood as a scan interval. The slab spacing may be provided by an axial displacement of a table or support (e.g., table 130). For example, a first rotation of the x-ray source 310 about an object to be imaged may be performed to obtain imaging information over the first slab length 302. Then the table or support may be translated the slab spacing 308 axially to move the object relative to the x-ray source 310. The slab spacing 308 may be understood as the difference between a first position at which the x-ray source 310 is disposed to perform a first scan and a second position at which the x-ray source 310 is disposed to perform a second scan. In the illustrated embodiment, the collimations for the scans are the same size, or provide an equal slab length, so the distance 309 between the top of the slabs is equal to the slab spacing 308. If the slab lengths 302, 304 are different, the source collimator 320 may be adjusted to provide the desired change in slab length. Once the table is positioned and the slab length configured, a second rotation of the x-ray source 310 at the new position may be performed to obtain imaging information over the second slab length 304. It may be noted that, in some embodiments, there may not be an overlap 306 between slabs. For example, one or more intermediate sections or portions may not be imaged, resulting in a gap or space between slabs.

As seen in FIG. 3, a seam 350 corresponds to the overlap 306 (e.g., the center of the overlap) of the first slab length 302 and the second slab length 304. The location of the seam 350 may be varied, for example, by adjusting one or more of the slab lengths 302 and 304 and/or the slab spacing 308. In various embodiments, collimation configurations may be selected to provide a seam location that provides for improved imaging. For example, if a seam 350 is located proximate a portion of anatomy that is particularly sensitive to radiation, the collimation configuration may be adjusted to move the seam 350 away from the sensitive portion of anatomy, so that the sensitive portion is exposed only during the collection of information over one slab instead of during the collection of information over two slabs. As another example, depending on the variation of opacity of portions of the anatomy being scanned, it may be desirable to position a seam 350 so that a portion of relative high opacity is contained within a single slab length, so that exposure to a higher radiation dosage (e.g., caused by tube current of an x-ray source) may be limited to one slab instead of two slabs. Thus, portions having a high opacity for which higher tube current may be desired may be grouped into one or more slabs for which a high tube current is used, while portions having a lower opacity may be grouped into one or more slabs for which a lower tube current is used, to limit use of higher tube current (and higher radiation dosage and/or noise) to appropriately sized and positioned slabs.

In FIG. 3, a primary scanning volume 360, shoulder regions 370, and scanning volume 380 are depicted. The primary scanning volume 360, shoulder regions 370, and scanning volume 380 are generally similar in respects to the primary scanning volume 240, shoulder region 250, and scanning volume 260 discussed in connection with FIG. 2. The primary scanning volume 360 corresponds to the volume included in the primary scanning volume of at least one slab, while the scanning volume 380 corresponds to the volume included in the scanning volume of at least one slab. The shoulder regions 370 are defined as the portions of the scanning volume 380 not included in the primary scanning volume 360.

The various scanning volumes resulting from a given collimation configuration (e.g., a collimation configuration selected by the processing unit 160) may be used to select collimation configurations, and/or identify collimation configurations for further evaluation by a user. FIG. 4 illustrates a scout image 400 with various scanning volumes overlayed on the scout image 400 that may, for example, be displayed to a user. The X-ray source and FOV's, for example, are not shown on FIG. 4 for clarity of illustration. A display similar to FIG. 4 may be provided to a user via a display unit (e.g., display unit 180), and may be used to receive confirmation that a selected collimation configuration provides an acceptable scanning volume, or that a different collimation configuration is desired. In FIG. 4, a scanning volume 410 resulting from a given collimation configuration is displayed. The scanning volume 410 includes a primary scanning volume 420 and shoulder regions 430. The primary scanning volume 420 and shoulder regions 430 may be displayed for example, with differing colors or tints associated with each for convenient identification by a user. The scanning volume 410 depicted in FIG. 4 is provided by two slabs, and includes a seam 440. As discussed herein, a user may view the scout image 400 with the scanning volume 410 overlayed, and determine if the scanning volume 410 is acceptable.

For example, in some embodiments, a target scanning region 470 may be identified based on a user input. For example, a user may select an upper boundary 472 (or a point along the upper boundary) and a lower boundary 474 (or a point along the lower boundary), as well as a diameter 476 (or a point along a diameter) corresponding to a width of the object to be contained within the target scanning region 470. In some embodiments, the user may also specify an offset distance from a central axis. The processing unit 160, as discussed in greater detail below, may then select a collimation configuration that provides a scanning volume (or, as seen in FIG. 4, the primary scanning volume 420) that contains the target scanning region 470. The scanning volume 410 may then be displayed to a user. If the user is satisfied with the scanning volume 410, the user may confirm the scanning volume 410 (and corresponding collimation configuration) and the collimation configuration may be used to perform a scan. However, if the user does not approve of the scanning volume 410 corresponding to the collimation configuration selected by the processing unit 160 (e.g., due to an undesired location of a seam, due to a portion of particular interest being located in the shoulder region 430 instead of the primary scanning volume 420, or the like) the user may request a different collimation configuration, and the processing unit 160 may determine an alternative collimation configuration and display the resulting scanning volume to the user.

Returning to FIG. 1, the adjustable source collimator 120 is configured to control the delivery of X-rays 114 from the X-ray source 110 to the object 102. In various embodiments, the adjustable source collimator 120 may be configured to be interposed between an X-ray source 110 and an object 102 to be imaged, and adjustable between plural settings corresponding to different amounts of collimation of x-rays 114 from the X-ray source 110 allowed to pass to the object 102. In the illustrated embodiment, the adjustable source collimator 120 is configured to adjust the size of the collimation length or slab length of radiation to which the object 102 is exposed. The collimation length or slab length in the illustrated embodiment corresponds to the length of the resulting FOV along the axial length of the table 130 at the center of a bore about which the X-ray source 110 rotates. In various embodiments, the adjustable source collimator 120 may include adjustable blades to adjust the slab length.

Figure 5:
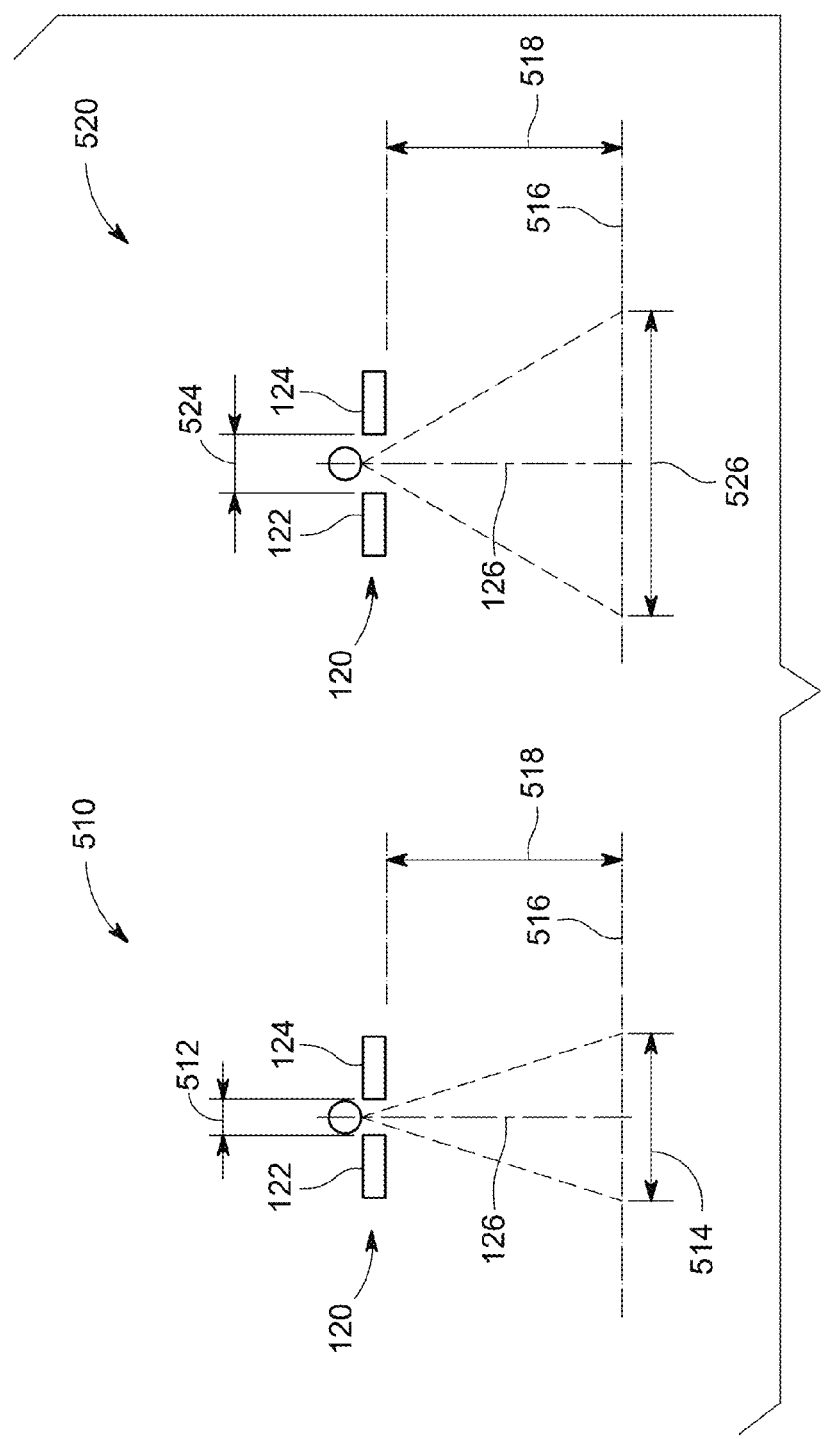
FIG. 5 illustrates example positions of an adjustable source collimator in accordance with an embodiment.

FIG. 5 illustrates example positions of the adjustable source collimator 120. The adjustable source collimator 120 includes a first blade 122 and a second blade 124 that are adjustable with respect to each other. For example, the first blade 122 and second blade 124 may be symmetrically adjustable with respect to a central axis 126 of a beam 128 allowed to pass through the adjustable source collimator. Because the imaging system 100 may include a number of sensitive components that need to be differently calibrated for each slab length, a limited number of different slab lengths may be provided. Thus, while the blades may be actuated by a mechanism that allows for continuous adjustment, in various embodiments, the adjustable source collimator 120 may be limited to a number of predetermined positions, providing for selection from available slab lengths. For example, the adjustable source collimator may be adjustable between a minimum slab length of about 40 millimeters, and a maximum slab length of about 160 millimeters. The adjustable source collimator 120 may be configured to be movable between positions corresponding to collimation lengths or slab lengths of about 40 millimeters, about 80 millimeters, about 120 millimeters, and about 160 millimeters. In various embodiments, other overall ranges of slab length or spacings between slab length settings may be employed.

Two example positions are shown in FIG. 5. At a first position 510, the first blade 122 and second blade 124 are set at a minimum blade distance 512 to provide a minimum slab length 514 at an axis 516 corresponding to the center of a bore about which an X-ray source associated with the adjustable source collimator 120 rotates. For example, the axis 516 may be disposed at a distance 518 from the first blade 122 and second blade 124. The minimum slab length 514 may be about 40 millimeters in various embodiments.

At a second position 520, the first blade 122 and the second blade 124 are still disposed at the distance 518 from the axis 518. However, the first blade 122 and the second blade 124 are set at a maximum blade distance 524 to provide a maximum slab length 526 in the second position 520. The maximum slab length 516 may be about 160 millimeters in various embodiments. Additional blade positions providing corresponding additional slab lengths may be provided between the first position 510 (or minimum slab length position) and the second position 520 (or maximum slab length position).

Returning to FIG. 1, the table 130 is configured to support the object 102 in a desired position, and is articulable in an axial direction 132. The table 130 is articulable in the axial direction 132 relative to the X-ray source 110 and adjustable source collimator 120. Thus, after a first slab of imaging information has been obtained, the table 130 may be translated a desired slab spacing distance along the axial direction 132 to provide for obtaining a second slab of imaging information. The number of slabs (e.g., number of times the table 130 is articulated along the axial direction 132) as well as the slab spacing (e.g., distance the table 130 is articulated along the axial direction 132) may be specified by the collimator configuration to be employed during a scan. In various embodiments, the table 130 may also be movable in a vertical direction (e.g., up and down as seen in FIG. 1) and/or in a lateral direction transverse to the axial direction 132 to center a portion of the object 102 to be imaged or otherwise positioning the object 102 in a desired position within the bore.

The depicted processing unit 160 is operably coupled to the input unit 170 and the adjustable source collimator 120. The processing unit 160 may include processing circuitry configured to perform one or more tasks, functions, or steps discussed herein. In various embodiments, the processing unit 160 may be configured to obtain a user input corresponding to a portion, region, or volume to be imaged, and to determine a prescribed collimation configuration to perform a scan of the portion, region, or volume to be imaged. The collimation configuration, for example, may identify one or more of a number of slabs to be obtained, the length of the slab(s), or spacing between slabs (scan interval). In some embodiments, the collimation configuration may also specify a radiation intensity (e.g., tube current) to be used for one or more slabs.

In various embodiments, the processing unit 160 may be configured to control one or more aspects of the imaging system 100 to implement a collimation configuration for a scan to be performed. For example, the processing unit 160 may be operably coupled to the adjustable source collimator 120 and configured to provide a control signal to the adjustable source collimator 120 to select a collimator or slab length (e.g., a signal positioning collimator blades 122, 124 in a position corresponding to a desired slab length). Further, the processing unit 160 may be operably coupled to the table 130 and configured to provide a control signal to the table 130 to position the table along the axial direction 132 (e.g., translate the table from a slab spacing distance from a first position corresponding to a first slab to a second position corresponding to a second slab). In some embodiments, the processing unit 160 may be operably connected to the X-ray source 110 and configured to provide a control signal to the X-ray source 110 (e.g., to control a tube current used for a given slab). Further still in some embodiments, the processing unit 160 may be configured to reconstruct an image using imaging information from the detector 150, and/or to provide imaging information from the detector 150 to an image reconstruction system for reconstructing an image.

Generally, in various embodiments, the processing unit 160 may be configured to determine a collimation configuration that provides a scanning volume that covers a target region corresponding to an input (e.g., a user input specifying a portion of the object 102 to be scanned). For example, the processing unit 160 may be configured to determine a target region based on one or more boundaries input by a user. The processing unit 160 may then determine a prescribed collimation configuration that provides a scanning volume corresponding to the target region. In some embodiments, the prescribed collimation configuration may provide a scanning volume (e.g., primary scanning volume along with shoulder regions) that encompasses the target region. In other embodiments, the determined collimation configuration may provide a primary scanning volume that encompasses the target region. In some embodiments, the prescribed collimation configuration is selected from a group of available collimation configurations (see, e.g., discussion herein regarding FIG. 6). In other embodiments, the prescribed collimation configuration may be determined by the processing unit 160 through use of a predetermined function. In various embodiments, the prescribed collimation configuration may be provided to a user prior to implementation of the prescribed collimation configuration to perform a scan, to allow the user to confirm the configuration, reject the configuration, or request a specified change or type of change to the configuration.

Generally, the processing unit 160 is configured to select a collimation configuration that will provide a scanning volume that satisfies predetermined criteria. For example, in addition to determining a collimation configuration that provides a scanning volume corresponding to a target region, the collimation configuration may be determined to satisfy or address one or more additional criteria. A collimation configuration may be selected to achieve or address one or more goals or objectives. For example, the one or more goals or objectives may include to minimize total collimation length (e.g., the sum of the slab lengths for all slabs of the configuration), to minimize dosage, to minimize total slabs used, to achieve a desired seam placement (or to avoid undesired seam placement), to group structures having similar opacity (and thus requiring similar source intensity/dosage/tube current) in common slabs, or the like. It may be noted that a given criterion may be a requirement in some embodiments (e.g., a collimation configuration providing the required coverage as well as the lowest radiation dosage may be selected as a rule regardless of other criteria), or, in other embodiments, may be given a preferential weighting relative to one or more other criteria.

In various embodiments, the processing unit 160 may be configured to have access to one or more lists of predetermined collimation configurations arranged in an hierarchical order from which the processing unit 160 selects the prescribed collimation configuration. For example, the processing unit 160 may be configured to use a given hierarchical listing based on input describing a scan to be performed. Thus, the criteria used to include and/or rank the entries in an hierarchical listing for one type of procedure may differ from another. Thus, one protocol may call for an hierarchical ranking based on radiation dosage, another based on collimation length, another based on seam placement, or the like. In some embodiments, a user may select the criterion or criteria on which the hierarchical listing is to be based, while in other embodiments a user may specify a procedure (e.g., cardiac scan) and the processing unit 160 select a corresponding predetermined hierarchical listing based on the selected procedure.

Figure 6:
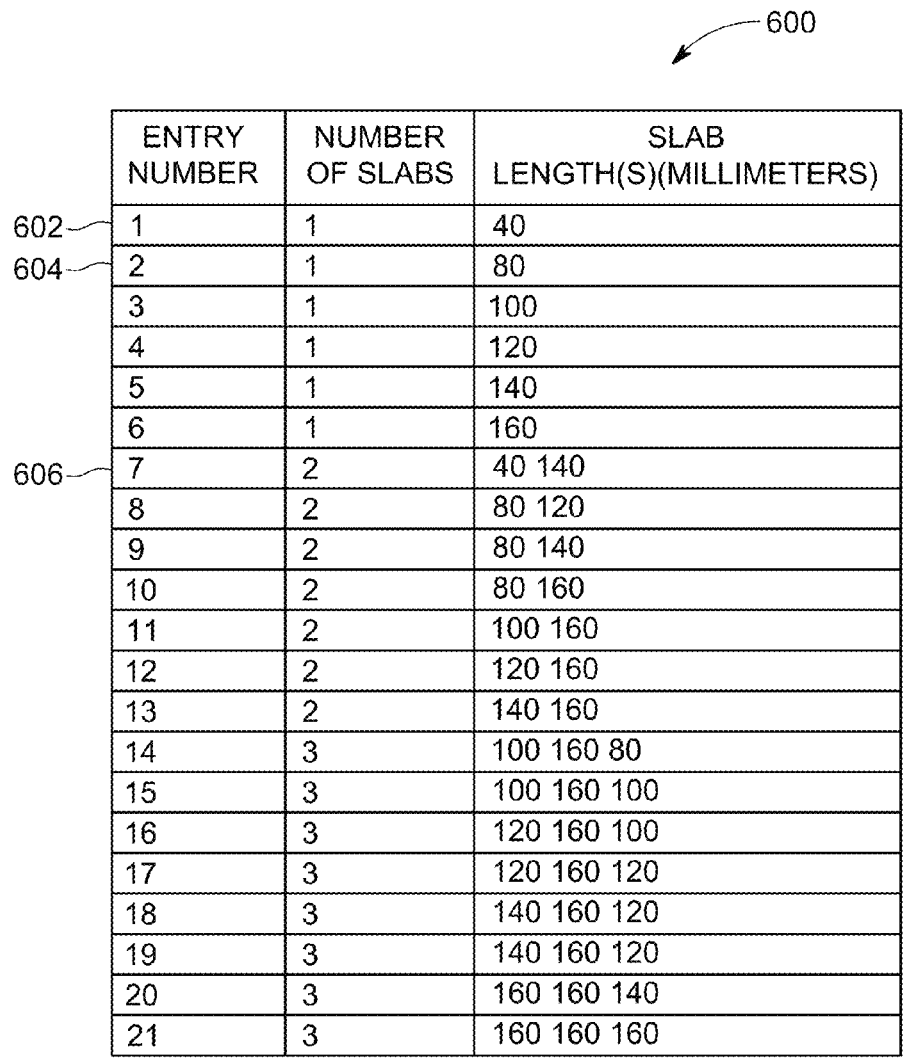
FIG. 6 provides an example hierarchical table used to select a collimation configuration in accordance with an embodiment.

FIG. 6 provides an example hierarchical table 600. In the embodiment depicted in FIG. 6, the collimation configurations are ranked by total collimation length in ascending order. The collimation configurations depicted in FIG. 6 are identified by the width of each slab in the collimation configuration. Thus, the first listed entry 602 corresponds to a single slab of about 40 millimeters width, the second entry 604 to a single slab of about 80 millimeters width, the seventh entry 606 to two slabs, the first of about 40 millimeters width and the second of about 140 millimeters width, and so on. In alternate embodiments, additional and/or alternative information may be listed. For example, the tube current used by the source for one or more slabs may be provided in some tables, with the listing ordered by total dosage. (It may be noted that a given collimator configuration may have a greater collimation width but a lower dosage than a configuration having a lower width, if the given collimator configuration has a sufficiently lower tube current over a relatively large range of the total collimation width.)

To use the hierarchical table 600, the processing unit 160 first determines a target scanning region, for example, based on user input. For example, the target scanning region may be determined based on input boundaries (e.g., upper, lower, diameter). The processing unit 160 then determines a scanning volume (e.g., primary scanning volume along with shoulder regions) provided by the collimation configuration of the first entry 602 in the hierarchical table 600. For example, the processing unit 160 may utilize a predetermined relationship between configuration and scanning volume based on table position and collimation width, or may have tabulated results for each collimation configuration detailing resulting primary scanning volumes, shoulder regions, and scanning volumes. Tabulated results may be stored, for example, as part of a database stored in a memory that is included with the processing unit 160 or otherwise accessible to the processing unit 160. The predetermined relationship and/or tabulated results may be based on past testing or results for a particular imaging system or type of imaging system. For configurations including multiple slabs, the processing unit 160 may determine the scanning volumes corresponding to the individual slabs, and then add or otherwise combine the resulting scanning volumes based on slab spacing to provide a composite scanning volume for the entire multi-slab configuration.

With the scanning volume for the first entry 602 determined, the processing unit 160 may next compare the resulting scanning volume to the target scanning region. If the scanning volume of the currently examined entry provides a desired amount of coverage (e.g., the scanning volume includes the target scanning region, the primary scanning volume includes the target scanning region, or the like) the currently examined entry is selected as the prescribed collimation configuration. Thus, if the scanning volume provided by the first entry 602 satisfies the selection criteria (e.g., adequate coverage of the target scanning region in this example), the first entry 602 is selected as the prescribed collimation configuration. If the scanning volume of the first entry 602 does not satisfy the selected criteria (e.g., the scanning volume does not include the complete target scanning region in this example), then the first entry 602 is rejected or disregarded, and the processing unit 160 determines the scanning volume resulting from the next configuration in the hierarchical order, in this case the second entry 604.

If the scanning volume of the second entry 604 satisfies the selected criteria, the second entry 604 is selected as the prescribed collimation configuration. If the scanning volume resulting from the second entry 604 does not satisfy the selected criteria (e.g., the scanning volume does not include the complete target scanning region in this example), then the second entry 604 is rejected or disregarded, and the processing unit 160 determines the scanning volume resulting from the next configuration in the hierarchical order, and so on.

It may be noted that the particular values and order depicted in FIG. 6 are provided by way of example, and that other values and/or orders of configurations may be employed in various embodiments. For example, in various embodiments, a processing unit 160 may be configured to use hierarchical orders tailored for particular procedures (e.g., a first hierarchical order for cardiac procedures, a second hierarchical order to scan the lungs, a third hierarchical procedure to scan the liver, a fourth hierarchical procedure to scan substantially the entire torso, and so on). Further, in some embodiments, the entries may be ranked according to total radiation dosage delivered for each collimation configuration. As another example, in some embodiments, configurations providing undesirable seam locations may be ranked relatively lower in the order, or omitted from the available selections.

In some embodiments, slab spacing, which may also be referred to as scan interval, may be varied as part of a selection process of a collimation configuration, and a collimation configuration having improved or optimal scan interval or slab spacing selected or determined. Smaller scan intervals correspond to more overlap between scans, and thus more radiation dose per total coverage, while larger scan intervals correspond to less overlap and less radiation per total coverage, but may provide, for example, gaps between the scanning volume and/or primary scanning volume that are undesirable. For example, in some embodiments, all or a portion of the entries in an hierarchical table may be ordered based on scan interval. A selection algorithm may start with the largest available scan interval and evaluate the available configurations until finding and selecting the configuration that provides the largest available scan interval while still satisfying one or more geometric constraints (e.g., all voxels of a desired imaging volume must be covered by at least one slab out to a specified diameter or width, all voxels of a desired imaging volume must be within the primary scanning volume, or the like). Optionally, a minimum acceptable scan interval may be set. Then, the selection algorithm may evaluate the available configurations in order of decreasing scan interval. As the scan interval decreases without finding a satisfactory configuration, a minimum scan interval may be reached. If the minimum scan interval is reached, the algorithm may then proceed to a different option or section of the hierarchical order (e.g., different number of slabs, different width of slabs, or the like).

Thus, the processing unit 160 may be configured to examine, in a predetermined hierarchical order, one or more entries in a list corresponding to available collimation configurations ordered according to one or more criteria, and select the highest ranked entry that includes a desired target scanning region as the prescribed collimation configuration. In some embodiments, the prescribed collimation configuration may automatically be implemented to perform a scan. In other embodiments, the prescribed collimation configuration may be displayed to a user (e.g., overlayed on a scout image), with the user having the option to confirm the prescribed collimation configuration (in which case the prescribed collimation configuration is implanted for the scan), or to reject or request modification of the prescribed collimation configuration. For example, if a prescribed collimation configuration is rejected, the processing unit 160 may identify the next highest ranked configuration of the listing that provides the desired scanning volume coverage as a prescribed collimation configuration to be presented to the user. In other embodiments, the user may specify one or more requested changes to the prescribed collimation configuration, such as movement of a seam, and the processing unit 160 may select a configuration accordingly.

Alternatively or additionally, the processing unit 160 may be configured to employ a function to determine the prescribed collimation configuration. For example, in various embodiments, a spatially-varying (in z, or along the axial direction 132) function may be employed that contains a weighted combination of one or more factors. The factors may include for example, a noise index, dose sensitivity of organs encountered in the scan (e.g., a seam corresponding to a double exposure proximate to the seam may be avoided over a dose-sensitive area), patient attenuation, sensitivity to misalignment (e.g., a seam over an organ prone to movement, such as the heart may be avoided to minimize registration difficulties between slabs), or sensitivity to contrast change (e.g., an organ such as the liver may be included in one slab). The various weights accorded to each factor may be adjusted based on a clinical objective (e.g., coronary assessment, pulmonary embolism detection, among others) and/or on patient demographic (e.g., age, gender, heart rate, contrast/renal sensitivity, breath hold duration ability). Thus, the coverage of axial collimation configurations may be optimized for a given set of criteria. It may be noted that, in some embodiments, the collimation configuration may also specify one or more helical pitches employed during a scan.

Various criteria that may be optimized to include, by way of example, number of slabs and/or time of scan, dosage, or image quality (IQ) (e.g., one or more of contrast uniformity, IQ uniformity, IQ resolution, or artifact avoidance). In some embodiments, the criteria used to select a prescribed collimation configuration may include specific targets or requirements of the relative volumes covered by the primary scanning volume and the shoulder regions. For example, the extension of the primary scanning volume and/or the shoulder region may be specified to a given radial distance, optionally as a function of axial position along the axial direction 132. As with the hierarchical ordering example discussed above, a prescribed collimation configuration determined using a weighted function may be automatically implemented (e.g., without user interference or approval) in some embodiments, or be presented to a user for confirmation or modification in other embodiments. For example, a user may request an adjustment based on a visual inspection of a scanning volume provided by a prescribed collimation configuration.

In some embodiments, seam location may be employed as a criterion, for example, to address radiation dosage and/or noise caused by tube current. For example, a seam may be undesirable in a particular region due to a possible transition in contrast dose over a given region. Alternatively or additionally, a seam may be undesirable due to potential misalignment of structures prone to motion. By including a structure prone to motion in a single slab, difficulties regarding registration between slabs obtained at different times may be reduced or eliminated. As another example, because seams correspond to an overlap between slabs, seams are associated with increased exposure and radiation dose. Thus, it may be desirable to position seams away from structures that are particularly dose sensitive.

In some embodiments, a noise or tube current metric along a z-direction (e.g., the axial direction 132) may be employed. For example, a slab having a relatively large length may deliver a high dose corresponding to a high tube current throughout the slab based on a required or desired tube current for a structure disposed along only a portion of the slab, as tube current may not varied over a single slab, but instead varied for different slabs. To avoid a high dose over the length of a relatively large slab, small slabs may be employed, each slab using a tube current appropriate for the structures within that particular slab, to lower overall dose and noise. Thus, an algorithm may be employed to select the most dose-efficient collimation for a given scan, and/or to balance dose efficiency with total number of slabs. It may also be noted that a dose reduction goal may not be limited to minimizing or reducing overall dose. For example, a goal may be to minimize a local dose, such as a dose to a sensitive organ. Or, a goal may be to minimize or reduce dose (local and/or total) while maintaining image quality (e.g., satisfying one or more image quality metrics). For example, a goal or objective may be the maximization or increase of a given image quality metric per dose level. In some embodiments, collimation configurations may be evaluated or selected based on a criterion of minimizing or reducing a time of scan. For example, reducing time of scanning may provide more uniform contrast enhancement within one or more regions.

It may be noted that trade-offs between criteria may be included as part of the weighting of criteria. For example, some embodiments may allow for a trade-off between number of total slabs and dose savings and/or dose efficiency, depending, for example, on the number of slabs and/or the amount of dose savings. For instance, a relatively low dose savings may be ignored to provide a minimum or reduced number of slabs, while a relatively high dose savings may be implemented despite resulting in an increased number of slabs.

The input unit 170 may be configured to obtain an input that corresponds to a portion of the object 102 to be imaged. As used herein, to "obtain" may include, for example, to receive. For example, in some embodiments, the input unit 170 may receive an input from a user entered via a touchscreen, keypad, mouse, voice or language recognition device, or the like. Alternatively or additionally, the input unit 170 may receive information from software configured to recognize one or more anatomical structures for example, from a scout image, with the target region specified to include identified anatomical structures of interest. Accordingly, in some embodiments the input may be a manual input or a user input, while in other embodiments the input may be entered in an automated or semi-automated fashion, for example using an automated or semi-automated segmentation algorithm. Further, in some embodiments, both user and automated inputs may be utilized, and/or a user may be provided with some amount of control or guidance with respect to an otherwise automated input. For example, an input generated automatically (e.g., a target region identified using an automated algorithm) may be displayed to a user and may be entered subject to user approval and/or modification.

User input provided to the input unit 170 may be provided in a variety of forms in various embodiments. For example, the user input may include one or more points corresponding to anatomy, such as point on a surface of a heart (e.g., as displayed in a scout image). As another example, the user input may include start and end locations on a z-axis (e.g., along the axial direction 132). The user input may also include one or more of a diameter or width of a desired volume to be imaged, an offset, or the like. The user input may also include constraints on the particular portion of the scanning volume that may include a given portion or portions of the desired imaging volume. For example, a user may input a constraint that a given point or points must be within the primary scanning volume, that a given point or points may be within a shoulder region but must be within a specified range of the primary scanning volume, or the like.

The input unit 170 may cooperate with the display unit 180 (and/or may form a single unit). For example, a scout image may be displayed on the display unit to a user. The user may then specify one or more boundaries based on the scout image (e.g., upper boundary, lower boundary, diameter or width). The processing unit 160 may determine a prescribed collimation configuration based on the target region, and display, via the display unit 180, the resulting scanning volume to the user. The user may confirm the prescribed collimation configuration, or request a change. In some embodiments, the processing unit 160 automatically cycles to the next appropriate entry in an hierarchical order, while in some embodiments the user may provide specific guidance regarding the requested change or criteria corresponding to the requested change. For example, the user may provide an input requesting movement of a seam a given distance, or, as another example, a request to include a selected location currently in a shoulder region into the primary scanning volume, or the like.

Thus, in various embodiments, a user may specify an upper and lower limit and diameter (e.g., distance from center of object) corresponding to the boundaries of a target region to be scanned, and the processing unit 160 may identify slab combination(s) that include the entire specified region within a primary scanning volume or within a scanning volume. As indicated above, in alternate embodiments, other inputs may be used to define the target region. For example, when an upper and lower boundary along with a diameter are specified, the target region may be understood as being generally rectangular when viewed in 2 dimensions and generally cylindrical when viewed in 3 dimensions. Other shapes of target regions (e.g., non-rectangular when viewed in 2 dimensions) may be utilized in other embodiments. In some embodiments, a user may be able to circle or otherwise enclose a selected target region on a displayed scout image using, for example, a touchscreen or stylus. As also indicated elsewhere herein, an input may be provided from an automated or non-human source. For example, a target scanning region may be determined using anatomic recognition software configured to analyze a scout scan. As one example, for a desired scan of the heart, a scout scan may be performed, and based on the scout scan, recognition software may identify a target scanning region to include the heart and any desired surrounding anatomy.

The display unit 180 is configured to provide information to the user. The display unit 180 may be configured to display, for example, a scout image having one or more scanning volumes associated with a collimation configuration (e.g., a prescribed collimation configuration). The display unit 180 may include one or more of a screen, a touchscreen, a printer, or the like.

Figure 7:
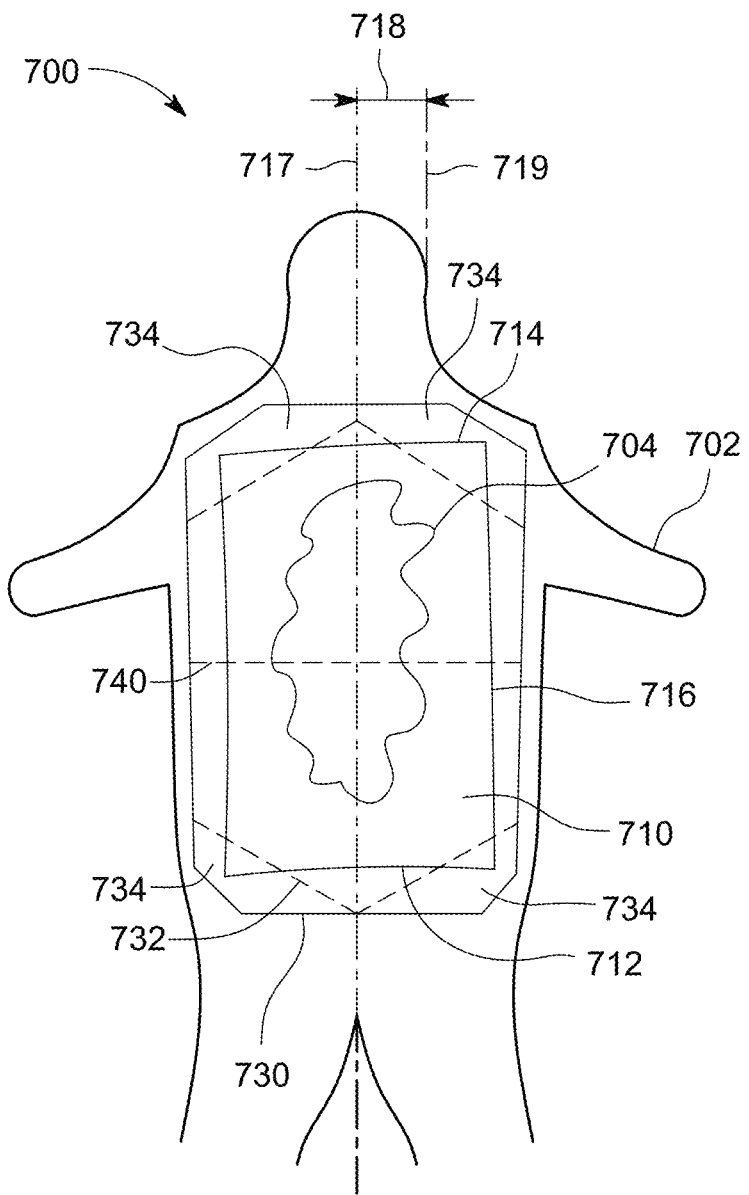
FIG. 7 illustrates a display provided to a user in accordance with an embodiment.

Use of the input unit 170 and display unit 180 in one example scenario will be discussed in connection with FIG. 7. In the example depicted in FIG. 7, a display 700 is provided to a user, for example on a screen of the display unit. The display 700 includes a scout image of a patient 702 including an anatomical structure of interest 704. The user may then specify, for example by touching a portion of a touchscreen, entering a location with a mouse, or the like, various conditions regarding a desired boundary within which scanning information is desired. For example, the user may specify one or more points or locations of an upper boundary 714 (e.g., by selecting a point on the upper boundary), one or more points or locations of a lower boundary 712 (e.g., by selecting a point on the lower boundary), a diameter 716, and/or an offset 718. The offset 718 may specify a distance separating the desired center 719 of the target region relative to a central axis 717 of the scout image. In the illustrated embodiment, no offset (e.g., an offset of zero) has been selected. The target region 710 may be determined by the processing unit 160 based on the upper boundary 714, the lower boundary 712, and the diameter 716 in the illustrated embodiment.

With the target region 710 now defined, the processing unit 160 may determine a prescribed collimation configuration as discussed herein. A scanning volume 730 corresponding to the prescribed collimation configuration may then be determined by the processing unit 160 and provided as part of the display 700. The displayed scanning volume 730 includes a primary scanning volume 732 and shoulder regions 734, as well as a seam 740. In the illustrated embodiment, the target region 710 is entirely contained within the scanning volume 730 but not entirely contained within the primary scanning volume 732, the anatomical structure of interest 704 is entirely contained within the primary scanning volume 732, and the seam 740 passes through the anatomical structure of interest 704. With the scanning volume 730 overlayed on the scout image 702, the user may inspect the coverage of the scanning volume 730 relative to the target region 710 and/or the anatomical structure of interest 704. If the scanning volume 730 is acceptable to the user, the user may input (e.g., via a keyboard, highlighted window on a touch screen, or the like) a confirmation, and the prescribed collimation configuration corresponding to the displayed scanning volume 730 may be used to perform a scan of the patient.

However, the user may reject the prescribed collimation configuration, and/or request a change. For example, the user may find the passage of the seam 740 through a central portion of the anatomical structure of interest 704 undesirable. The user may then request (e.g., via a keyboard entry, selection from a pull down menu, or the like) a movement of the seam 740 a given distance to prevent the seam 740 from passing through the anatomical structure of interest 704. Additionally or alternatively, the user may not approve of the inclusion of portions of the target region 710 in the shoulder regions 734 instead of being entirely within the primary scanning volume 732. The user may then request a scanning volume 730 that includes one or more points in the primary scanning volume 732 (e.g., identified by touching a portion of the display desired to be within the primary scanning volume 732). Thus, in various embodiments, a scanning volume 730 corresponding to a prescribed collimation configuration determined (e.g., selected) by the processing unit 160 may be presented to the user and iteratively modified until a final collimation configuration is confirmed (e.g., approved by the user).

Figure 8:
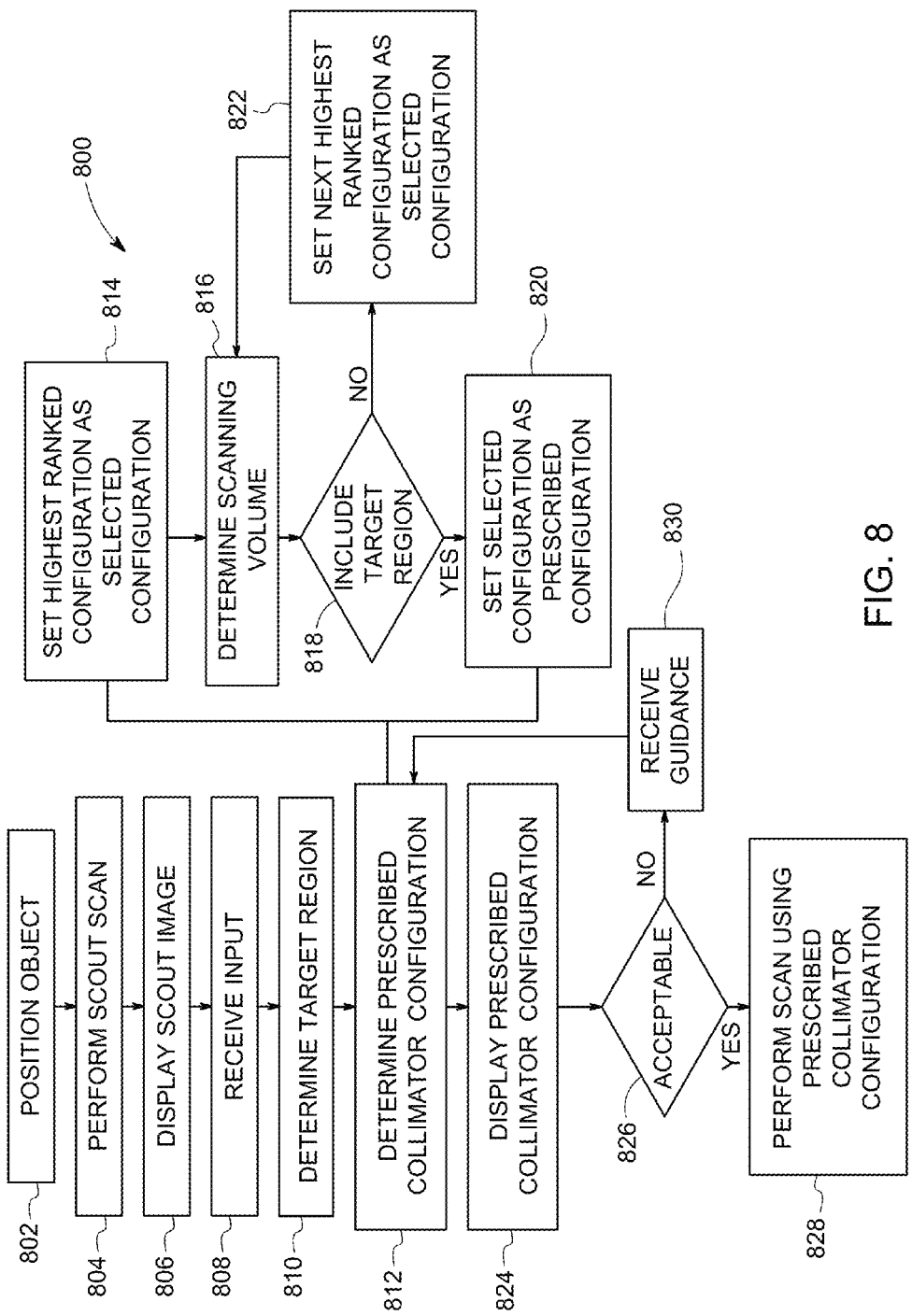
FIG. 8 is a flowchart of a method in accordance with an embodiment.

FIG. 8 provides a flowchart of a method 800 for selecting a collimation configuration for imaging an object (e.g., obtaining a CT image of the object). The method 800, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 800 may be able to be used as one or more algorithms to direct hardware (e.g., one or more aspects of the processing unit 160) to perform one or more operations described herein.

At 802, an object to be imaged is positioned. For example, the object may be a human patient positioned on a table (e.g., table 130) in the bore of a CT imaging system.

At 804, a scout scan is performed, and the scout image is displayed at 806. At 808, an input is received. As one example, the input may be received from a user, or, as another example, may be received from an algorithm configured to select or determine a portion of an object to be scanned. For example, using the displayed scout image as a reference, the user may specify one or more boundaries corresponding to a desired target scanning region corresponding to a portion of the patient for which an image is desired. The input may specify one or more locations or points of an upper boundary, lower boundary, diameter, or offset. The input may provide a specific predetermined shape, such as an outline provided via a touchscreen by the user. Alternatively or additionally, the boundary may be indicated by an input received from software configured to identify anatomical structures from a scout image, and/or according to a predetermined protocol for a given procedure.

At 810, a target region is determined. The target region corresponds to a volume for which imaging information is desired to be obtained and for which an image is desired to be reconstructed. For example, the target region may be determined by a processing unit (e.g., processing unit 160) based on the input received at 808.

At 812, a prescribed collimation configuration is determined. The prescribed collimation may be determined by a processing unit (e.g., processing unit 160) to provide a corresponding scanning volume (e.g., scanning volume or primary scanning volume) that includes the target region determined at 810. The prescribed collimation configuration may be determined to satisfy or address one or more additional criteria, such as minimizing or reducing number of slabs, minimizing or reducing radiation dosage, or the like.

Substeps 814-820 provide one example of determination of a collimation configuration. In substeps 814-820, a prescribed collimation configuration is selected from an ordered list of available collimation configurations. The ordered list is configured to order the available collimation configurations based on one or more predetermined criteria, such as total collimation width, total radiation dosage, or the like.

At 814, the highest ranked (e.g., the first) listed collimation configuration is set as a selected collimation configuration (e.g., by a processing unit such as processing unit 160). At 816, a scanning volume (e.g., a primary scanning volume along with shoulder regions) is determined (e.g., by a processing unit) for the selected collimation configuration. At 818, the scanning volume determined at 816 is compared to the target region determined at 810. If the scanning volume includes the target region, the currently selected collimation configuration is set as the prescribed collimation configuration at 820. If the scanning volume determined at 816 does not entirely contain the target region, the method proceeds to 822. At 822, the current collimation configuration is discarded and the next highest ranked available collimation configuration is set as the selected collimation configuration, and the method returns to 816. Thus, the available collimation configurations may be evaluated serially in an order of desirability based on one or more selection criteria to select the highest ranked configuration that provides adequate coverage of the target region.

At 824, the prescribed collimation configuration is displayed to a user. For example, a scanning volume provided by the prescribed collimation configuration may be provided on a screen, for example overlayed on a scout image. In some embodiments, attributes or characteristics of the prescribed collimation configuration may be displayed. For example, the display may list one or more of total slabs, slab length for each slab, radiation dosage, identification of seam location, or the like.

At 826, it is determined if the prescribed collimation configuration is acceptable. For example, a user may visually compare a displayed scanning volume corresponding to the prescribed collimation configuration and determine if the displayed scanning volume is satisfactory.

If the scanning volume and corresponding collimation configuration are acceptable, the method proceeds to 828. At 828, a scan is performed using the prescribed collimation configuration. If the scanning volume is not satisfactory, the method returns to 812 and a different collimation configuration is determined. In the illustrated embodiment, at 830, guidance is received for selecting the replacement collimation configuration. For example, a user may specify a desired change, such as a change in slab length for one or more slabs, a reduction in total slabs, movement of a seam, or the like. In other embodiments, guidance may not be received, and the processing unit 160 may, for example, resume examination of the remaining members of a previously employed hierarchical order or listing.

Thus, various embodiments provide for improved selection or determination of collimation configurations. For example, traditional systems may merely assume that a particular scan range will be available for each collimation, and that a fixed overlap is used when two or more adjacent regions are scanned, without regard to the reconstruction limits or anatomic constraints and/or image quality constraints. In contrast, various embodiments discussed herein determine collimation configuration as a function of a desired image volume (e.g., by determining scanning volumes corresponding to available collimation configurations and selecting a configuration that includes the desired image volume). Various embodiments also address one or more additional criteria in the determination of a collimation configuration. Various embodiments discussed herein provide for selection among different overlaps between adjacent slabs and/or different combinations of number of slabs and slab length.

Figure 9:
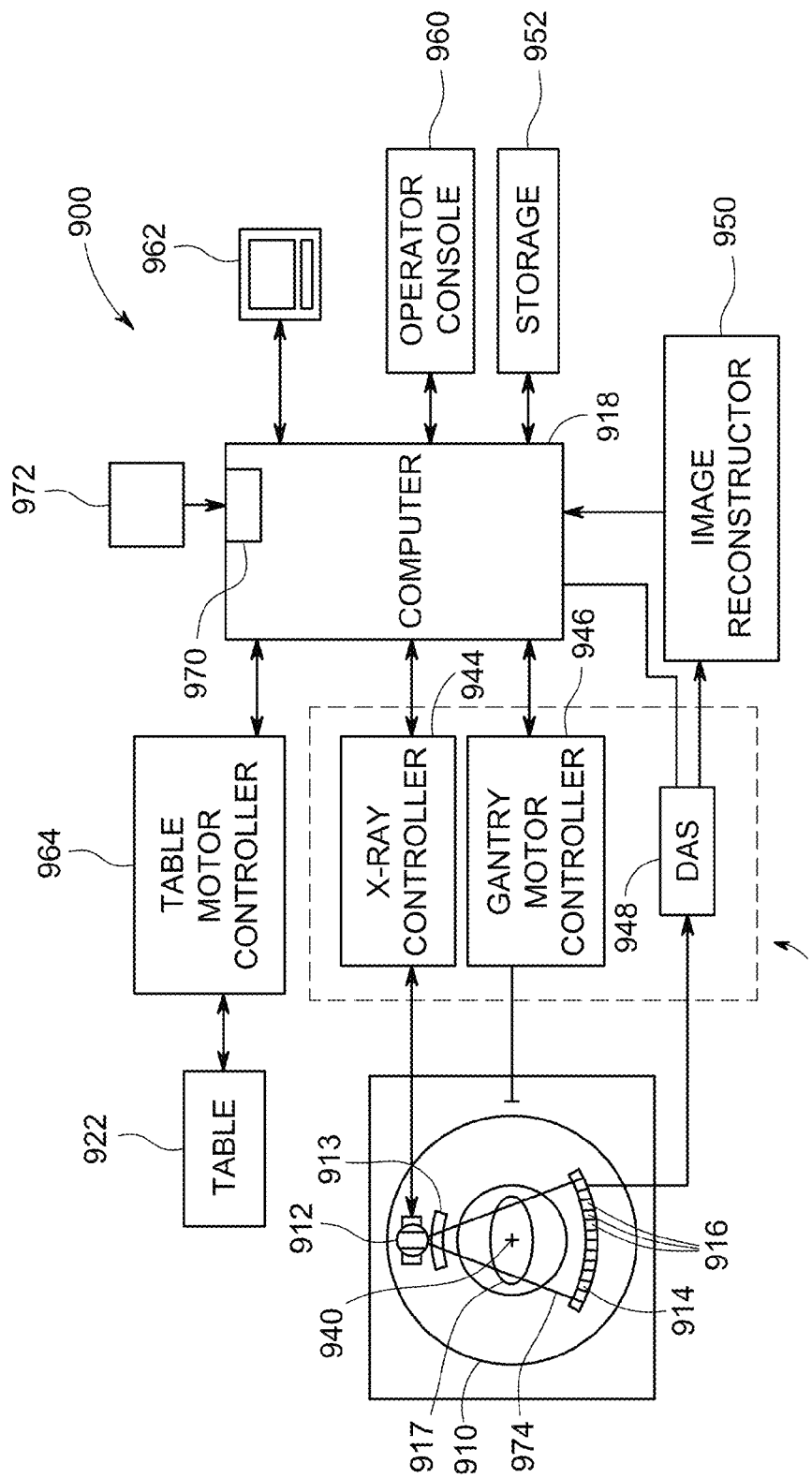
FIG. 9 is a schematic block diagram of a computed tomography (CT) imaging system in accordance with an embodiment.

Various methods and/or systems (and/or aspects thereof) described herein may be implemented using a medical imaging system. For example, FIG. 9 is a block schematic diagram of an exemplary CT imaging system 900 that may be utilized to implement various embodiments discussed herein. Although the CT imaging system 900 is illustrated as a standalone imaging system, it should be realized that the CT imaging system 900 may form part of a multi-modality imaging system. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam 974 of X-rays toward the detector array 914 on the opposite side of the gantry 910. A source collimator 913 (e.g., adjustable source collimator 120) is provided proximate the X-ray source 912. The detector array 914 includes a plurality of detector elements 916 that are arranged in rows and channels that together sense the projected X-rays that pass through a subject 917. The CT imaging system 900 also includes a computer 918 that receives the projection data from the detector array 914 and processes the projection data to reconstruct an image of the subject 917. In operation, operator supplied commands and parameters are used by the computer 918 to provide control signals and information to reposition a motorized table 922. More specifically, the motorized table 922 is utilized to move the subject 917 into and out of the gantry 910. Particularly, the motorized table 922 moves at least a portion of the subject 917 through a gantry opening (not shown) that extends through the gantry 910. Further, the motorized table 922 may be used to move the subject 917 from a first position corresponding to a first slab to a second position corresponding to a second slab.

As discussed above, the detector array 914 includes a plurality of detector elements 916. Each detector element 916 produces an electrical signal, or output, that represents the intensity of an impinging X-ray beam 974 and hence allows estimation of the attenuation of the beam as it passes through the subject 917. During a scan to acquire the X-ray projection data, the gantry 910 and the components mounted thereon rotate about a center of rotation 940. FIG. 9 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from the plurality of detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the motorized table 922 moves at least a portion of the subject 917 through the gantry opening.

In various embodiments, the computer 918 includes a device 970, for example, a floppy disk drive, CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a floppy disk, a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view". A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation. Thus, in some embodiments, a scan (or slab) corresponding to a 360 degree view may be obtained using less than a complete revolution.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. An imaging system comprising:
    an X-ray source;
    an adjustable source collimator configured to be interposed between the X-ray source and an object to be imaged, the adjustable source collimator adjustable between plural settings corresponding to different amounts of collimation of x-rays from the X-ray source;
    an input unit configured to obtain an input identifying a portion of the object to be imaged; and
    a processing unit operably coupled to the input unit and the adjustable source collimator, the processing unit configured to:
        obtain the input; and
        determine a prescribed collimation configuration for the adjustable source collimator to perform a scan of the portion to be imaged based on the input, the prescribed collimation configuration having a corresponding scanning volume that includes the portion to be imaged, wherein the processing unit is configured to select the prescribed collimation configuration using a hierarchical list of configurations ranked according to at least one predetermined criteria.

2. The imaging system of claim 1, wherein the processing unit is configured to start with a configuration having the largest available scan interval and evaluate the available configurations until finding and selecting the prescribed collimation configuration that provides the largest available scan interval while still satisfying one or more geometric constraints.

3. The imaging system of claim 1, wherein each collimation configuration of the hierarchical list of configurations specifies a total number of slabs to be imaged and a collimation length for each slab to be imaged, wherein the group of predetermined collimation configurations includes slabs of different lengths.

4. The imaging system of claim 1, wherein the processing unit is configured to select the prescribed collimation configuration from the hierarchical list of configurations to provide a minimum available total collimation length that provides coverage of at least the scanning volume.

5. The imaging system of claim 1, wherein each of the configurations from the hierarchical list of configurations further comprises an x-ray source intensity corresponding to each slab of the corresponding predetermined collimation configuration, and wherein the processing unit is configured to select the prescribed collimation configuration from the hierarchical list of configurations to provide a minimum dosage that provides coverage of at least the scanning volume while satisfying an image quality condition.

6. The imaging system of claim 1, wherein the processing unit is configured to select the prescribed collimation configuration based on a seam location of adjacent slabs provided by the prescribed collimation configuration.

7. The imaging system of claim 1, wherein the input comprises a user input comprising an identification of at least two points from a user.

8. The imaging system of claim 1, wherein the X-ray source is configured to rotate around the object to be imaged, wherein the scanning volume includes a primary scanning volume and a shoulder region, the primary scanning volume corresponding to a volume including locations receiving 360 degrees of exposure as the X-ray source performs a rotation around the object, the shoulder region corresponding to at least one volume that does not receive 360 degrees of exposure but receives sufficient exposure to provide a clinically useful image for the at least one volume, wherein the input comprises a user input comprising an identification of at least one point in one of the primary scanning volume or the shoulder region, wherein the at least one predetermined criteria includes at least one criteria corresponding to relative volumes covered by the primary scanning volume and the shoulder region.

9. The imaging system of claim 1, further comprising a display configured to display the scanning volume corresponding to the prescribed collimation configuration to a user, wherein the input unit is further configured to receive at least one of a confirmation of the displayed scanning volume or a request for modification of the displayed scanning volume.

10. The imaging system of claim 9, wherein the X-ray source is configured to rotate around the object to be imaged, wherein the scanning volume includes a primary scanning volume and a shoulder region, the primary scanning volume corresponding to a volume including locations receiving 360 degrees of exposure as the X-ray source performs a rotation around the object, the shoulder region corresponding to at least one volume that does not receive 360 degrees of exposure but receives sufficient exposure to provide a clinically useful image for the at least one volume, and wherein the displayed scanning volume is configured to display the primary scanning volume and the shoulder region, wherein the at least one predetermined criteria includes at least one criteria corresponding to relative volumes covered by the primary scanning volume and the shoulder region.

11. A method for selecting a source collimation configuration for an object to be imaged, the method comprising:
receiving, at an input unit, an input identifying a portion of the object to be imaged; and
determining, with a processing unit, a prescribed collimation configuration for an adjustable source collimator to perform a scan of the portion to be imaged based on the input, the prescribed collimation configuration having a corresponding scanning volume that includes the portion to be imaged, wherein determining the prescribed collimation configuration includes selecting the prescribed collimation configuration using a hierarchical list of configurations ranked according to at least one predetermined criteria.

12. The method of claim 11, wherein the determining a prescribed collimation configuration comprises starting with a configuration having the largest available scan interval and evaluate the available configurations until finding and selecting the prescribed collimation configuration that provides the largest available scan interval while still satisfying one or more geometric constraints.

13. The method of claim 11, wherein the prescribed collimation configuration is selected from the hierarchical list of configurations to provide a minimum available total collimation length that provides coverage of at least the scanning volume.

14. The method of claim 11, further comprising displaying, to a user, the scanning volume corresponding to the prescribed collimation configuration, the method further comprising receiving, at the input unit, at least one of a confirmation of the displayed scanning volume or a request for modification of the displayed scanning volume.

15. The method of claim 14, wherein the scanning volume includes a primary scanning volume and a shoulder region, the primary scanning volume corresponding to a volume including locations receiving 360 degrees of exposure as an X-ray source performs a rotation around the object, the shoulder region corresponding to at least one volume that does not receive 360 degrees of exposure but receives sufficient exposure to provide a clinically useful image for the at least one volume, wherein the method further comprises displaying the primary scanning volume and the shoulder region to the user, wherein the at least one predetermined criteria includes at least one criteria corresponding to relative volumes covered by the primary scanning volume and the shoulder region.

16. A tangible and non-transitory computer readable medium configured to select a source collimation configuration for an object to be imaged, the tangible and non-transitory computer readable medium comprising one or more computer software modules configured to direct one or more processors to:
receive an input identifying a portion of the object to be imaged; and
determine, automatically, a prescribed collimation configuration for an adjustable source collimator to perform a scan of the portion to be imaged based on the input, the prescribed collimation configuration having a corresponding scanning volume that includes the portion to be imaged, wherein the prescribed collimation configuration is selected using a hierarchical list of configurations ranked according to at least one predetermined criteria.

17. The tangible and non-transitory computer readable medium of claim 16, wherein the tangible and non-transitory computer readable medium is further configured to direct the one or more processors to select the prescribed collimation configuration by starting with a configuration having the largest available scan interval and evaluating the available configurations until finding and selecting the prescribed collimation configuration that provides the largest available scan interval while still satisfying one or more geometric constraints.

18. The tangible and non-transitory computer readable medium of claim 16, wherein the prescribed collimation configuration is selected from the group of predetermined collimation configurations to provide a minimum available total collimation length that provides coverage of at least the scanning volume.

19. The tangible and non-transitory computer readable medium of claim 16, wherein the tangible and non-transitory computer readable medium is further configured to direct the one or more processors to display the scanning volume corresponding to the prescribed collimation configuration and to receive, responsive to the display of the displayed scanning volume, one of a confirmation of the displayed scanning volume or a request for modification of the displayed scanning volume.

20. The tangible and non-transitory computer readable medium of claim 19, wherein the scanning volume includes a primary scanning volume and a shoulder region, the primary scanning volume corresponding to a volume including locations receiving 360 degrees of exposure as an X-ray source performs a rotation around the object, the shoulder region corresponding to at least one volume that does not receive 360 degrees of exposure but receives sufficient exposure to provide a clinically useful image for the at least one volume, wherein the tangible and non-transitory computer readable medium is further configured to direct the one or more processors to display the primary scanning volume and the shoulder region to the user.

* * * * *